United States Patent [19]

Boisde et al.

[11] 4,403,861
[45] Sep. 13, 1983

[54] PHOTOMETRIC ANALYZER FOR AUTOMATICALLY STUDYING COMPLEX SOLUTIONS

[75] Inventors: Gilbert Boisde, Bures sur Yvette; Claude Bonnejean, Ris Orangis; Jean J. Perez, Chatillon, all of France

[73] Assignee: Commissariat a l'Energie Atomique, Paris, France

[21] Appl. No.: 220,971

[22] Filed: Dec. 29, 1980

[30] Foreign Application Priority Data

Jan. 23, 1980 [FR] France ................................ 8001408

[51] Int. Cl.³ .............................................. G01J 3/50
[52] U.S. Cl. .................................... 356/407; 356/414; 356/419
[58] Field of Search ............... 356/402, 405, 406, 407, 356/408, 414, 416, 419

[56] References Cited

U.S. PATENT DOCUMENTS

| | | | |
|---|---|---|---|
| 3,582,664 | 6/1971 | Hrdina | 356/419 |
| 3,690,772 | 9/1972 | Endl | 356/416 |
| 3,770,354 | 11/1973 | Tsuruta et al. | 356/407 |
| 3,819,277 | 6/1974 | Berthelot et al. | 356/414 |

Primary Examiner—Vincent P. McGraw
Attorney, Agent, or Firm—Pearne, Gordon, Sessions, McCoy, Granger & Tilberry

[57] ABSTRACT

The present invention relates to a photometric measuring device making it possible to automatically study complex solutions with variable "background noise."

This device comprises a light source (2) making it possible to illuminate a measuring cell, means for splitting the light beam (20, 22) from source (2) into a plurality of individual beams, balancing means (24), means (26) for selecting each wavelength associated with each of the light beams, a discriminator (28) making it possible to distinguish the different wavelengths, means (26) for making the light beams monochromatic, detection means (46) and an analog computing system (44) making it possible to calculate the concentration of several dissolved chemical species.

Application to the following or monitoring of chemical reactions.

9 Claims, 21 Drawing Figures

FIG.4 III

FIG. 10 III

FIG. 10 IV

PHOTOMETRIC ANALYZER FOR AUTOMATICALLY STUDYING COMPLEX SOLUTIONS

BACKGROUND OF THE INVENTION

The present invention relates to a photometric measuring device making it possible to automatically study complex solutions with variable "background noise."

More specifically, the invention relates to a device making it possible to sequentially or quasi-continuously determine the concentration of several chemical species contained in the same solution. This device more particularly makes it possible to follow the concentration variations of these chemical species, e.g. during a dilution, a chemical reaction, a solvent-extraction, a reduction in the strength of the concentration of one or more species in the bath, etc. This solution can have a varying turbidity and/or contain parasitic chemical species which may or may not constitute a variable background noise. These parasitic chemical species can, for example, be constituted by the progressive fouling of the walls or cells or photometric measuring vessels by the solutions under investigation which are never perfectly clear or can be the by-products of chemical reactions, e.g. during the following or monitoring of a chemical reaction. This is generally the case with industrial solutions.

At present, numerous types of colorimeters, photometers or spectrophotometers are known for the purpose of measuring the concentration of dissolved chemical species by applying the Beer-Lambert law.

Photometric determinations which several wavelengths are already covered by numerous patents and the corresponding equipment is commercially available.

Differential photometric analysis with two wavelengths is also known, making it possible to eliminate a background noise or turbidity, assumed to be identical at the two measuring wavelengths. For further details on this differential measurement with two wavelengths, reference can be made, for example, to French Pat. No. 2,106,754, filed on Sept. 23rd 1970 by the COMMISSARIAT A L'ENERGIE ATOMIQUE and entitled "Photometric analyser with two wavelengths for the determination of elements in a solution."

Devices also exist which, for remote measurements, give details by means of optical fibres of the concentration of $n-1$ chemical species by means of n wavelengths. Calculations provide details on the concentration of these $n-1$ chemical species and the device is described in French Pat. No. 2,317,638, filed on July 9th 1975 by the COMMISSARIAT A L'ENERGIE ATOMIQUE and entitled "Device for analysing the constituents of a solution by photometric measurement."

At present, the various devices for measuring the concentration of a dissolved chemical species use a system of references necessary for the determination of the optical density and therefore the concentration of said chemical species. This reference device uses, for example, a reference solution which only contains the pure chemical species or a "sampling blank" linked with the solvent absorbing power. For a chemical species dissolved in a solvent, the "sampling blank" is generally formed from said pure solvent.

Moreover, the uses of which devices are limited. Thus, in the case of a high light absorption by the chemical species, the optical density or absorption associated with the species can assume a considerable value. The optical density value is dependent not only on the extinction coefficient of the chemical species, but also the concentration in solution of said species. Under these conditions, it is necessary to sample the solution and perform the necessary number of dilutions, this generally being the case for industrial solutions highly concentrated in one or more chemical species.

In order to permit a direct study of the concentration of the different chemical species in solution, i.e. obviating any sampling of the solution which is a nuisance when monitoring a reaction, it is advantageous to be able to carry out the determination of these concentrations by using a device able to work not only on the absorption peaks, but also on the sides and even the toes of the curves of the absorption spectrum plotted beforehand. The presently known devices are not very suitable for determining the optical density on the sides and toes of curves.

BRIEF SUMMARY OF THE INVENTION

The object of the present invention is to obviate these disadvantages and in particular make possible the elimination of a system of references, whilst providing the possibility of working on the sides and toes of absorption spectrum curves, thereby obviating any sampling of the solution.

The present invention relates to a photometric measuring device making it possible to automatically study complex solutions with variable "background noise."

According to the invention, this device comprises:
the regulated light source making it possible to illuminate by means of an adequate optical system a measuring cell which can contain a solution to be studied;
means for splitting the light beam from the source into n individual light beams in which n is an integer higher than 2;
balancing means making it possible to balance the light intensity of the n light beams;
means for selecting each predetermined wavelength associated with each of the n light beams;
a discriminator making it possible to distinguish the n wavelengths from one another;
means for making the n light beams monochromatic;
detection means able to transform the light received into an electrical signal;
an analog computing system making it possible to calculate the concentration of at the most $n-1$ chemical species present in the solution;
means for the visual display of the results.

According to an essential feature of the invention, the analog computing system has a modular characteristic making it possible to calculate an expression of form:

$$K \log \frac{(I)_\alpha}{(I)_\beta}$$

in which k represents an attenuation coefficient $(I)_\alpha$, the light intensity corresponding to the wavelength $\lambda_{60}$ and $(I)_\beta$ the light intensity corresponding to the wavelength $\lambda_\beta$.

This mathematical expression follows from a simplification of the differential measurement utilized in the device according to the invention. Thus, the automatic balancing before any measurement of the initial optical transmissions $(I_o)_\alpha$ and $(I_o)_\beta$ associated respectively with the wavelengths $\lambda_\alpha$ and $\lambda_\beta$, such that:

$$\log \frac{(I_o)_\alpha}{(I_o)_\beta} = 1$$

obviates the measurement of a "sampling blank" and also the compensation of scale zero. However, it is necessary to use a well regulated light source in order that its relative stability is ensured at the wavelengths. In this case, the resultant differential optical density becomes:

$$+\Delta D = D_\alpha - D_\beta = \log \frac{(I)_\beta}{(I)_\alpha}$$

in which $D_\alpha$ represents the optical density associated with the wavelengths $\lambda_\alpha$ and $D_\beta$ the optical density associated with the wavelength $\lambda_\beta$.

When the measurement of a chemical species has an absorption peak, partly obscured by a variable "background noise," generally the determination of the optical density associated with this species is determined by means of a so-called Allen correction. For determining the optical density corresponding to the chemical species under these conditions, three wavelengths are used, namely a measuring wavelength and two reference wavelengths and in this connection reference can be made to French Pat. No. 2,317,638. Generally, it is rare for the absorption spectrum of one chemical species to be symmetrical to the absorption peak and, when used, said correction remains approximate. However, its generalization can be made in the absence of symmetry of the absorption spectrum.

Thus, it is possible to demonstrate that in general terms, no matter what the choice of the wavelengths $\lambda_1, \lambda_2$ and $\lambda_3$, the measurement of the dissolved species is given by:

$$C = K \left[ \log \frac{I_3}{I_2} + k \log \frac{I_1}{I_2} \right]$$

in which C represents the concentration of the species, k a coefficient dependent on the device and the solution to be studied and k a proportionality coefficient dependent on the three selected wavelengths $\lambda_1, \lambda_2$ and $\lambda_3$. This expression is based on the Beer-Lambert law and the simplification of the differential measurement referred to hereinbefore.

According to a preferred embodiment of the invention, this device comprises means for selecting each wavelength and means for making each light beam monochromatic, being constituted by fixed interference filters corresponding to a given wavelength gap ($\lambda \pm \Delta \lambda$) and adapted to the desired type of measurement.

According to a preferred embodiment of the invention, the device comprises means for selecting each wavelength and means for making each light beam monochromatic, being constituted by monochromators.

The use of fixed interference filters for monochromators makes it possible to work on any part of the absorption spectrum and in particular on the sides and toes of the absorption spectrum curve. The differential measurement making it possible to eliminate a background noise or turbidity can be carried out between the sides or toes of the absorption spectrum curves. Therefore, it is possible to utilize the absorption spectrum of a chemical species with two or three wavelengths on the same side of the absorption peak. This corresponds to the extrapolation of the Allen correction. Mathematical analysis makes it possible to show that the concentration of the chemical species, which it is desired to determine, is given by an expression of the same type as that given hereinbefore. Under these conditions, the attenuation coefficient k can be positive or negative.

However, it should be noted that this type of correction can only be applied for spectrally known species. For concentrated solutions, the determination of the concentration by measurement at the curve toe is strict if the Beer-Lambert law is proved at three selected wavelengths, even in the presence of turbidity or a constant background noise. The same applies for a variable background noise according to the Beer-Lambert law using interference filters or monochromators well adapted to the interfering species. In this case, the coefficient k still requires a precalibration.

This type of calculation makes it possible to determine at the curved toe concentrations of chemical species whose absorption is too high at the absorption peak. This is often the case with industrial solutions, where the concentration of the dissolved chemical species is high. Moreover, this type of calculation makes it possible to eliminate a variable or non-variable background noise which can interfere with the chemical species to be determined.

The use of three wavelengths makes it possible to analyse either two chemical species with turbidity deduction, or a single chemical species with a correction of the variable or non-variable background noise in the studied spectral band.

In the case of two chemical species interfering with the variable background noise, it is necessary to adopt a fourth wavelength. Under these conditions, the concentration of these two chemical species is given by a mathematical expression of the same type as that referred to hereinbefore with a supplementary term of the following type:

$$K \log \frac{(I)_\alpha}{(I)_\beta}$$

in which, as hereinbefore, $(I)_\alpha$ is the light intensity associated with the wavelength $\lambda_\alpha$ and $(I)_\beta$ the light intensity associated with the wavelength $\lambda_\beta$. This justifies the modular nature of the analog computing system.

According to a preferred embodiment of the invention, the discriminator making it possible to distinguish the different wavelengths from one another is constituted by a first, solid half-cylinder of limited thickness not permitting the passage of light and whereby to the centre of the flat part of said half-cylinder is fixed a plane mirror and a second half-cylinder of the same size as the first and having three holes made in the rounded part of said second half-cylinder positioned in such a way that the light of a light beam entering by one of these holes is reflected by the plane mirror and leaves by another hole, there being at least three such holes.

Moreover, this discriminator is able to rotate about its axis with a continuous movement in such a way as to permit, following the processing of light and then electrical information, to display curves of the concentration variation over a period of time of the at the most $n-1$ chemical species present in the solution to be studied.

According to another preferred embodiment of the invention, the discriminator making it possible to distinguish the different wavelengths from one another is constituted by a first member able to rotate with respect to a second fixed member in which are located n optical fibres, one of the ends of each of these fibres issuing to the outside of said second member facing the first member, the first member being provided with an opening which can be brought selectively in front of the said end of each of the optical fibres, the latter being joined to form a single optical fibre and at their other end so as to connect the discriminator to the detection means, then constituted by a single detector making it possible to sequentially determine the concentration of the at the most n−1 chemical species present in the solution to be studied.

The device for locating the light beam from the discriminator is electrically connected to the analog computing system and makes it possible to start the calculations associated with said beams.

BRIEF DESCRIPTION OF THE DRAWINGS

The invention is described in greater detail hereinafter relative to non-limitative embodiments and the attached drawings, wherein show.

DETAILED DESCRIPTION OF THE PREFERRED EMBODIMENTS

Figure 1:
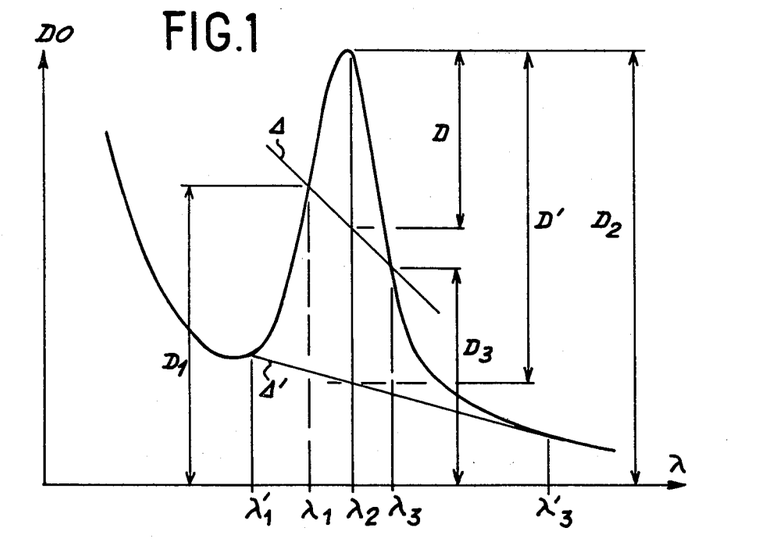
FIG. 1 the Allen correction and its generalisation on a random absorption spectrum.

FIG. 1 shows an absorption spectrum giving the optical density (O.D) or absorption as a function of the wavelength ($\lambda$). The Allen correction consists of taking two wavelengths $\lambda_1$ and $\lambda_3$ at an equal distance and on either side of the absorption peak corresponding to the wavelength $\lambda_2$. The background noise is likened to a linear function with the wavelength (straight line $\Delta$). Thus, the concentration of this species is proportional to the resultant optical density D such that:

$$D = D_2 - \frac{D_1 + D_3}{2}$$

with $D_1$, $D_2$, $D_3$ being the optical densities corresponding respectively to the wavelengths $\lambda_1, \lambda_2, \lambda_3$.

The generalisation of the Allen correction consists of performing the same calculation by taking two wavelengths $\lambda_1'$ and $\lambda_3'$, selected on either side of the wavelengths $\lambda_2$, but in a random manner. The background noise is likened to a linear function with the wavelength (straight line $\Delta'$). The concentration of the species is proportional to the resultant optical density $D'$.

Figure 2:
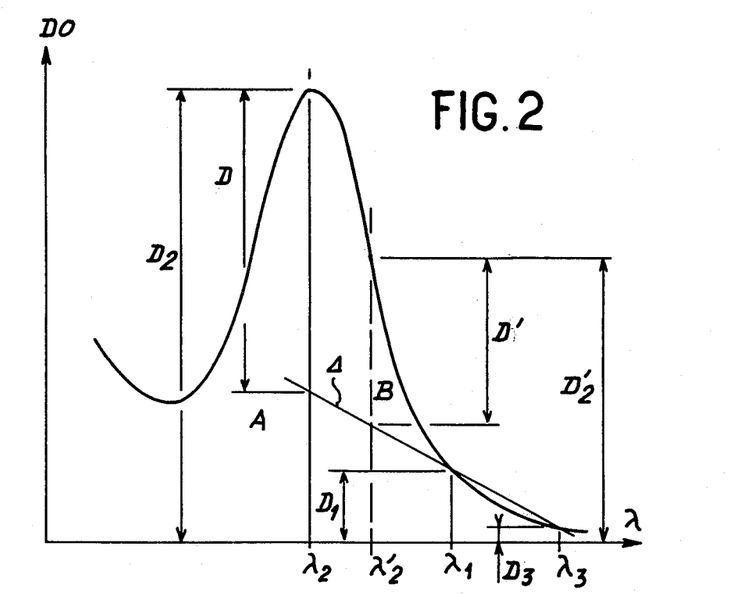
FIG. 2 the extrapolation of the Allen correction on a random absorption spectrum.

FIG. 2 shows another absorption spectrum. The extrapolation of the Allen correction consists of taking two wavelengths $\lambda_1$ and $\lambda_3$ on the same side of the absorption peak corresponding to wavelength $\lambda_2$ for example, to the right of the absorption peak and at the curve toe. The line $\Delta$ defined by the optical densities $D_1$ and $D_3$ associated with the wavelengths $\lambda_1$ and $\lambda_3$ is extrapolated up to point (A). The concentration of the chemical species is then proportional to the optical density D. In order to determine the concentration of this species, it is also possible to use the optical density $D'$, corresponding to the extrapolation of the line $\Delta$ up to point (B) for a wavelength $\lambda_2'$ taken on a side of the absorption peak. This can advantageously be used when the absorption peak does not appear on the spectrum (highly concentrated or highly absorbent species).

Figure 3:
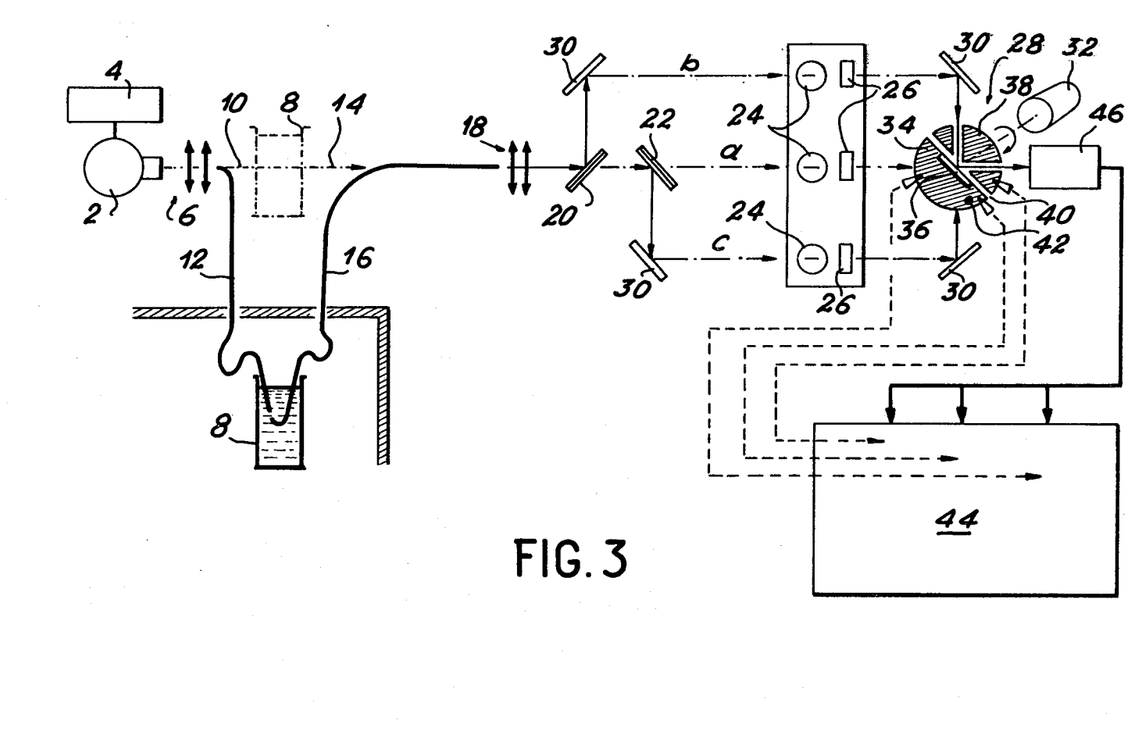
FIG. 3 an overall diagram of a three-channel device according to the invention.

FIG. 3 shows an overall diagram of a three-channel device. A light source 2, regulated by means of a device 4, transmits, via lenses 6, a white light beam to a measuring cell 8, with manual filling or circulation, either directly 10 or by means of an optical fibre 12. The measuring cell 8 which can contain the solution to be analysed is an optical cell of conventional design up to an optical path of 5 cm or of special design above 5 cm. The light beam leaving cell 8 can be directly transmitted 14 or by means of an optical fibre 16 permitting, for example, remote measurements over the remainder of the device. In the case of corrosive products, it is possible to combine flexible and rigid optical fibres (French Pat. No. 2,317,638).

The light from cell 8 is transformed into homogeneous light spots by a system of lenses 18. Two splitting plates 20 and 22, inclined by 45° with respect to the beam from the source make it possible to form three light beams a, b, c. Balancing systems 24 (optical wedge, iris, etc.) make it possible to balance the light energies of the three channels. A system of fixed interference filters 26 or monochromators is placed in front of a discriminator 28 which can rotate about its axis in a continuous or discontinuous manner. The three light beams a, b, c are directed at the discriminator 28 by means of plane mirrors, such as 30. Discriminator 28 is rotated by means of a motor, such as 32.

This rotary discriminator 28 comprises a first solid half-cylinder 34 of limited thickness, which does not permit the passage of light and to which is fixed in the centre of the flat part a plane mirror 36 and a second half-cylinder 38 of the same size as the first half-cylinder and having holes 40 made in the rounded part of the second half-cylinder. These holes 40 are positioned in such a way that the light of one of the light beams a, b or c enters by one of the holes, is reflected by the plane mirror 36 and leaves by another hole 40. There are four holes 40 in the case of a three-channel discriminator 38. This rotary discriminator 28 comprises a locating or marking device making it possible to locate the light beam which is reflected by mirror 36. This locating device can be constituted, for example, by a hole 42 made in the half-cylinder 36 of the rotary discriminator 28. When discriminator 28 rotates, the hole 42 is placed alternately in front of three not shown optoelectronic systems. Each of these systems is associated with one of the three beams a, b, c reaching the discriminator 28.

This locating device is electrically connected to the analog computing system 44 and makes it possible to initiate the calculations associated with the beam reflected by mirror 36 of the rotary discriminator 28. A single detector 46 makes it possible to transform the light received into an electrical signal and is connected to the analog computing system 44.

Figure 4:
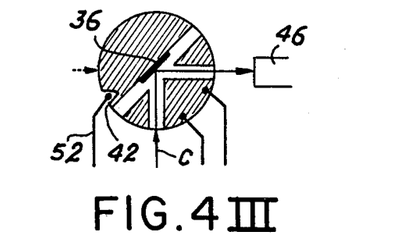
FIG. 4 diagrammatically, the different positions of the discriminator according to a first variant for a three-channel device.
Figures 4, 4I:
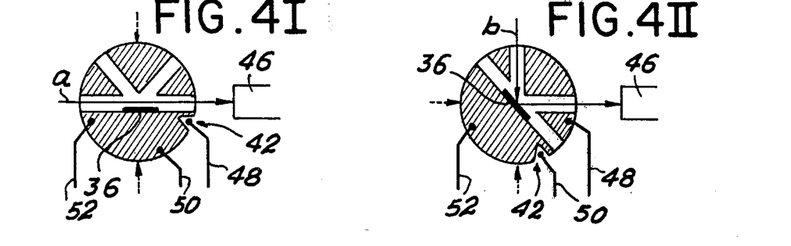

FIG. 4 shows the different positions of the rotary discriminator for a three-channel device. This type of device makes it possible to analyse two dissolved chemical species with turbidity deduction or a single chemical species with correction of a variable or invariable background noise.

FIG. 4-I shows the passage through the discriminator 28 of the single beam a. This light beam a illuminates detector 46. Beam a is located by means, for example of a hole 42 and an opto-electronic device designated by the reference numeral 48.

FIG. 4-II shows the passage through discriminator 28 of beam b, reflected by mirror 36 and illuminating detector 46. Beam b is located, for example, by means of a hole 42 and an opto-electronic device 50.

FIG. 4-III shows the passage through discriminator 28 of beam c, reflected by mirror 36 and reaching detector 46. Beam c is located by means, for example, of the hole 42 and an opto-electronic device 52.

FIG. 4-IV shows the passage of beam a, not located by the opto-electronic device 48. This passage can be taken into account for the calculations, particularly in the case of optical background noise or black current.

Through the use of a rotary discriminator 28 and an opto-electronic locating device functioning in the aforementioned manner, it is possible to use only a single detector 46 as the detection means.

Figure 5:
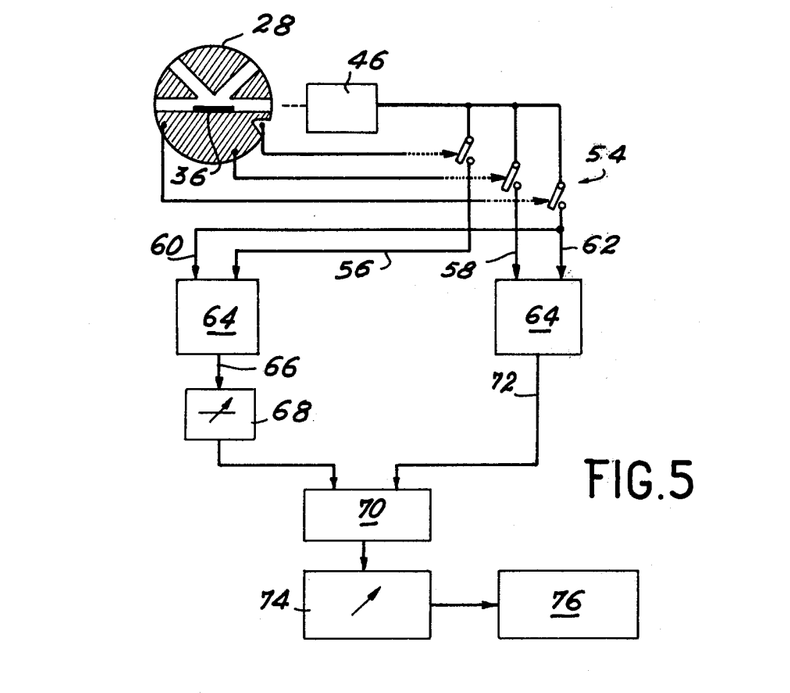
FIG. 5 diagrammatically, the analog computing system according to the invention.

FIG. 5 diagrammatically shows the analog computing system. The aforementioned locating device makes it possible to start the calculations associated with the beam and reflected by mirror 36 of discriminator 28 by means of switches such as 54. This diagrammatically shown analog computing system 44 makes it possible to calculate the mathematical expressions of the type given hereinbefore. The electrical signals from detector 46 corresponding, for example, to a light intensity $I_1$ associated with the wavelength $\lambda_1$ reach 56. The electrical signals corresponding, for example, to a light intensity $I_2$ associated with the wavelength $\lambda_2$ reach 60 and 62. The electrical signals corresponding for example, to a light intensity $I_3$ associated with the wavelength $\lambda_3$ reach 58. These electrical signals are amplified by means of logarithmic inverting amplifiers 64. The expression, for example:

$$\log(I_1/I_2)$$

obtained for its inverse reaching 66 is multiplied by the attenuation factor k by means of a multiplier 68. The mathematical expression then obtained is added by means of an adder 70 to an expression of type:

$$\log(I_3/I_2) \text{ (or its inverse)}$$

reaches 72. The expression obtained at the output of adder 70 is then multiplied by a coefficient k by means of a multiplier 74. The final results obtained corresponding to the concentration of one or more predetermined chemical species is then displayed by means of a device 76, for example a recorder. When discriminator 28 rotates about its axis with a continuous movement after processing of the light data by detector 46 and then the electrical data by the analog computing system 44, point by point curves of the variation of the concentration over a period of time of the different chemical species present in the solution to be studied, appear on recorder 76.

Figure 6:
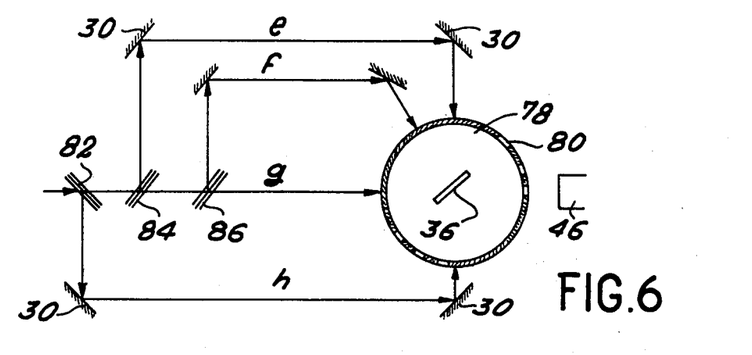
FIG. 6 diagrammatically, part of a four-channel device according to the invention.

FIG. 6 diagrammatically shows part of a four-channel device. This device makes it possible to analyse three dissolved chemical species with turbidity deduction or two chemical species with correction of a variable or invariable background noise.

The four-channel discriminator 78 is represented differently compared with that with three channels. Obviously, any other form can be envisaged. This four-channel discriminator 78 has six holes 80 grouped into two groups of three in the same half-cylinder constituting discriminator 78. The latter is provided in its centre with the plane mirror 36. Four light beams e, f, g, h directed by means of mirrors such as 30 which reach discriminator 78. These four beams are obtained by splitting a single beam by means of the splitting plates 82, 84, 86 oriented by an angle of 45° with respect to the incident beam. As hereinbefore the light data from discriminator 78 are converted into an electrical signal by means of a detector 46. The locating system of the light beam reflected by mirror 36, as well as the analog computing system 44 must be modified compared with those of the three-channel device.

Figure 7:
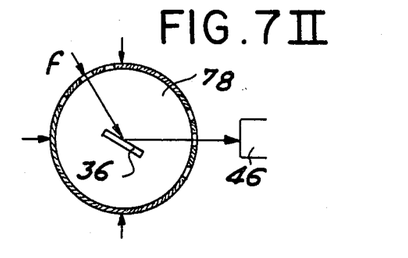
FIG. 7 diagrammatically, the different positions of the discriminator according to a first variant for a four-channel device.
Figure 7I:
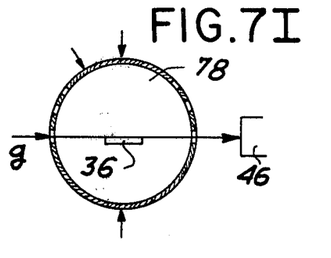

FIG. 7 shows the different positions of a rotary discriminator for a four-channel device.

FIG. 7-I shows the passage of beam g through discriminator 78, the light intensity of beam g being received by a detector 46.

FIG. 7-II represents the passage of light beam f through discriminator 78, said light beam e being reflected by mirror 46 onto detector 36.

FIG. 7-III represents the passage of light beam e through discriminator 78, said light beam e being reflected by mirror 36 onto detector 46.

FIG. 7-IV represents the passage of light beam h through discriminator 78, said light beam h being reflected by mirror 36 onto detector 46.

Figure 8:
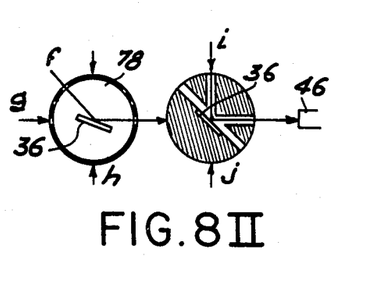
FIG. 8 diagrammatically, two discriminators arranged in cascade according to a first variant.
Figure 8I:
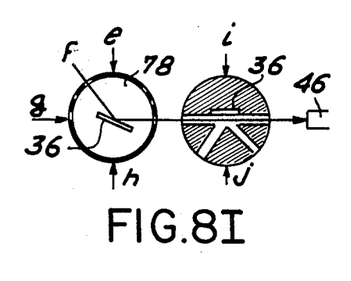

FIG. 8 shows two rotary discriminators arranged in cascade form. It is possible to see the combination of a rotary four-channel discriminator 78 and a rotary three-channel discriminator 28. Discriminator 78 permits the passage in the direction of the detector of beams such as e, f, g, h in the same way as hereinbefore, provided that the discriminator 28 is positioned correctly and at stop (FIG. 8-I). However, discriminator 28 only alternately permits the passage of two light beams, e.g. i and j provided that no beam leaves discriminator 28 (FIG. 8-II).

Figure 9A:
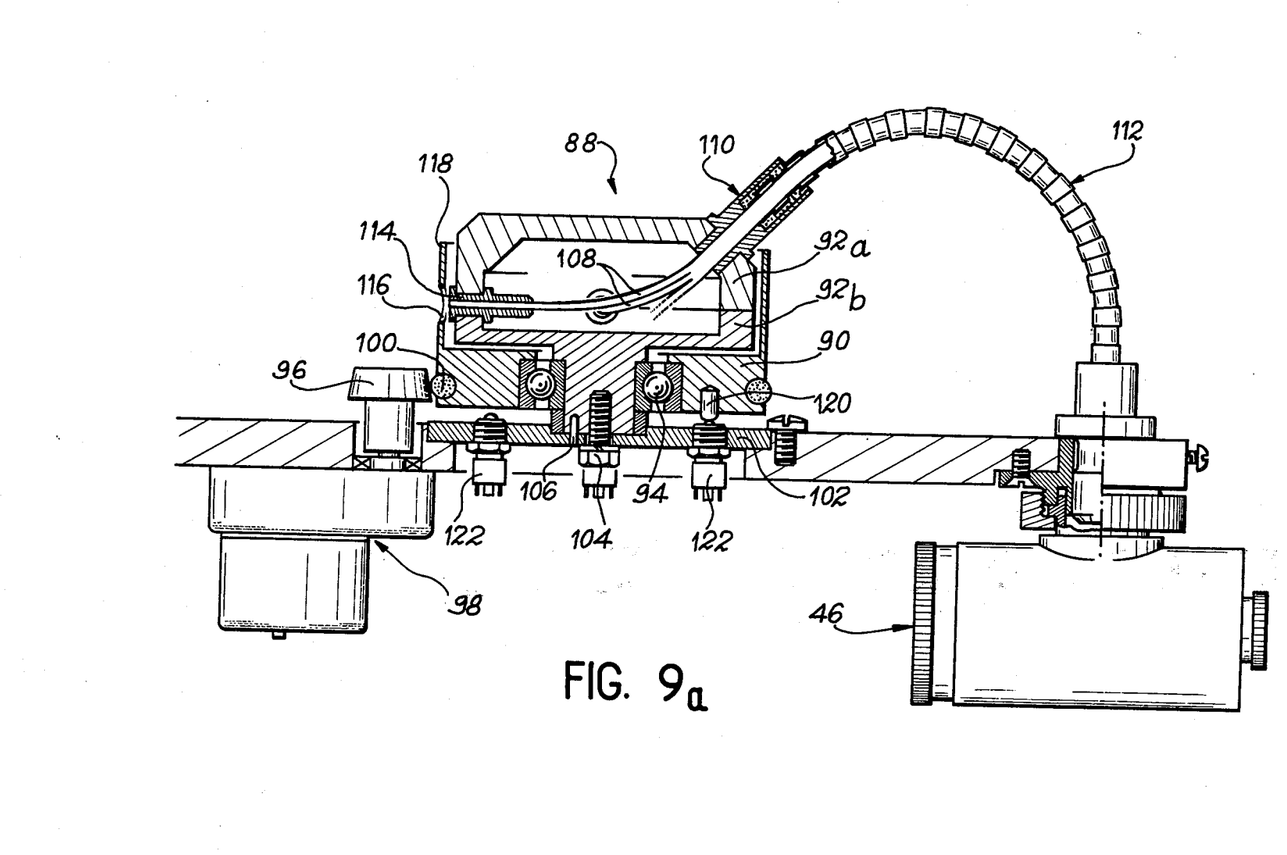
FIG. 9 diagrammatically, a discriminator for a three-channel device according to a second variant.
Figure 9B:
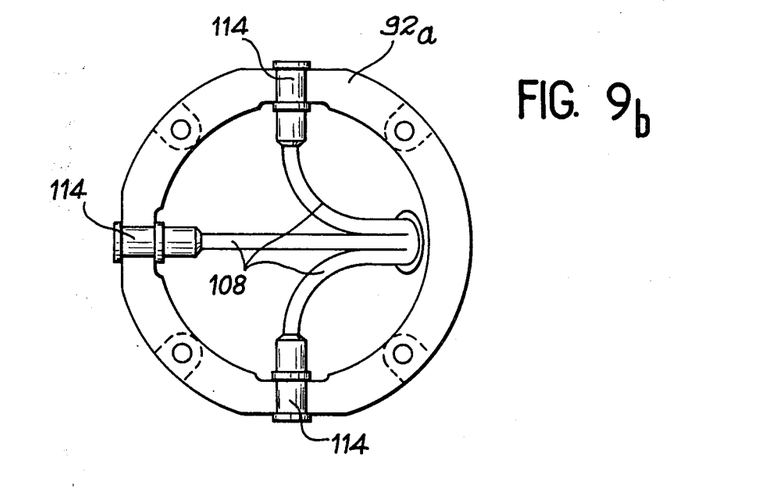

FIG. 9 shows another embodiment of a rotary-three-channel discriminator 88 (FIG. 9a) which comprises a first member 90 able to rotate with respect to a second fixed member 92, e.g. a cylindrical member, by means of a ball bearing 94. A rod 96 connected to a reduction gear 98 makes it possible to rotate first member 90 by friction on an O-ring 100. The second member 92 mounted on a plate 102 which is detachable by means of screws 104 and is held in place on said plate by means of pins 106, contains three optical fibres such as 108, one of whose ends is connected by means of an appropriate connector 110 to a single sheathed optical fibres 112 terminating in front of detector 46 and whose other sheathed ends 114 pass to the outside of said second member and face the first member 90. Ends 114 can, for example, be arranged radially (FIG. 9b). Member 92 can be formed from two portions 92a, 92b in such a way that the fitting of optical fibres 108, 112 is facilitated.

The first member 90 is provided with an opening 116, for example on an annular portion 118, thereof surrounding the second member 92 and which can selectively be brought in front of end 114 of optical fibres 108. When the end 114 of one of the three optical fibres 108 faces opening 116, the light beam associated with said fibre is transmitted by means of the sheathed fibre 112 to detector 46. When member 90 is rotated, the different light beams are successively transmitted to detector 46.

The light beam leaving discriminator 88 can be located by means of a pin 120 integral with the rotary member 90, which comes into contact with one of the switches 122. These four switches 122, integral with plate 102 are, for example, arranged at 90° from one another and face each optical fibre. Switches 122 are electrically connected to the analog computing system 44 and make it possible to start the calculations associated with the light beam leaving discriminator 88.

Figure 10:
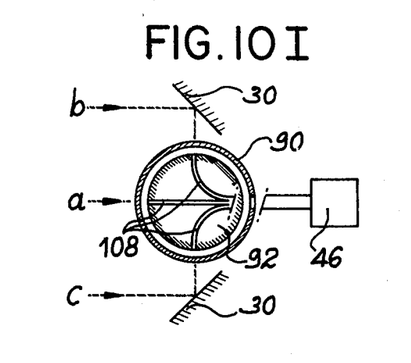
FIG. 10 diagrammatically, the different positions of the discriminator of FIG. 9.

FIG. 10 shows the different positions of such a discriminator.

In FIG. 10-I, none of the light beams a, b or c has been transmitted to the detector 46.

FIG. 10-II shows the passage of beam b through discriminator 98, the light intensity of said beam being received by detector 46.

FIGS. 10-III and 10-IV respectively show the passage of the single beam a and c through discriminator 88.

Obviously, the configuration of the discriminator and also the number of its channels are dependent on the number of dissolved chemical species, the presence of a background noise or the presence of turbidity. Moreover, when there is a large number of channels, a plurality of discriminators with 2, 3, 4 and more channels can be arranged in cascade.

The device according to the invention is of simple design and makes it possible to perform original calculations. As a result of this device, it is possible to directly determine in line the concentration of several chemical species present in the same solution, no matter what complexity of the solution or the concentration of the different chemical species. Due to the fact that this device can work on the sides and toes of curves where the optical density value is lower than at the absorption peak, it is possible to study highly concentrated chemical species. The concentration of the different species appears in the form of point by point curves, when the discriminator rotates continuously. Obviously, the distance between two consecutive points is dependent on the discriminator rotation speed. For certain industrial controls of the concentration variation of the different chemical species over a period of time, it is necessary to obtain continuous curve plotting. Under these conditions, it is always possible to stop the discriminator and use several detectors (one for each wavelength) as detection means.

In other words, when a single sequential photometric measurement is sufficient, the properties of the rotary discriminator associated with a single detector are used. Conversely, when a continuous photometric measurement is necessary (e.g. sudden variation of the concentration of one or more chemical species), the number of detectors is a function of the wavelengths necessary for calculating the concentration of the chemical species present in the solution under study. Under these conditions, discriminator 28, equipped with its mirror, is able to reflect the light of the n light beams striking the latter towards the n detectors. Moreover, a four-channel discriminator, like discriminator 28, only permits the analysis of two chemical species with turbidity deduction or a single chemical species with background noise correction, instead of the three chemical species with turbidity deduction or two chemical species with background noise correction.

When it is desired to know the concentration of one or more chemical species, for example, interfering with a background noise or of high absorption, it is necessary to calibrate the device so as to ascertain the linearity between the absorption and the concentration (Beer-Lambert law) and so as to determine the attenuation coefficients k (function of the wavelengths used) and K dependent on the device and the solution under study.

The device according to the invention has been tested with uranium(VI) in a 2 N nitric medium. After balancing the channels, the first corresponding to a wavelength of 418 nanometers for the absorption peak, the second to a wavelength of 449 nanometers for the side and the third to a wavelength of 530 nanometers, the Beer-Lambert law was proved for the ratio 530/418,
530/449,
449/418. This confirms the possibility of using an interference filter for measurement on the sides of the absorption peak.

This is obviously only an example and it would also have been possible to use other wavelengths selected, for example, on a curved toe. The relative absorptions at 449 and 418 nanometers on the one hand and 530 and 549 on the other are respectively $22.2 \cdot 10^{-3} C$ and $12.3 \cdot 10^{-3} C$/cm of optical path, in which C is the concentration in g/l.

The device was also tested with uranium(VI) in the present of iron(III) at different concentrations in a 2 N nitric solution. It should be noted that iron (III) interferes with uranium(VI). The determination of iron(III) in the 2 N nitric medium shows that the Beer-Lambert Law is followed up to a concentration of 4 g/l, which is the maximum concentration for the retreatment solutions. The relative absorptions between 449 and 418 nanometers on the one hand and between 530 and 449 nanometers on the other give respectively $6.1 \cdot 10^{-3} C$ and $0.2 \cdot 10^{-3} C$, in which C is the iron (III) concentration in g/l.

By means of what has been stated hereinbefore, it is possible to deduce the uranium concentration in the presence of iron(III). The application of an attenuation coefficient k to the highest relative absorption of the interfering element provides a good evaluation of the uranium concentration by resolving two equations with two unknowns:

$$10^3 \cdot D_{418}^{449} = 22.2 \, C_U + 6.1 \, C_{Fe} \text{ and}$$

$$10^3 \cdot D\frac{530}{449} + 12.3 \, C_U + 0.2 \, G_{Fe}$$

which gives:

$$C_U = K \left[ D_{449}^{530} - 0.028 \, D_{418}^{449} \right]$$

The design of the apparatus makes it possible to directly adjust the coefficient k=0.28 by a potentiometer and then obtain a concentration recording by adjusting the coefficient k.

The determination of the uranium concentration is obtained with a relative error of 5% for a concentration of 1.5 g/l of uranium(VI) in the presence of 4 g/l of iron(III).

For constant or known acidity, it is finally possible to demonstrate that it is possible to measure the iron in the presence of uranium, which is an advantage of the device. It is merely necessary to exchange the multiplication factor in accordance with the formula:

$$\log \frac{I_{449}}{I_{418}} + k \log \frac{I_{449}}{I_{530}} \text{ with } k < 1.$$

In the same way, it has been possible to demonstrate that uranium can be analysed in solutions having a variable acidity. For this purpose, it is merely necessary to have three wavelengths for determining on the one hand the uranium concentration with acidity correction and on the other the concentration in total nitrates (i.e. the nitric acid concentration) by a calculation of the type:

$$[NO_3] = K \frac{\log \frac{I_3}{I_2} + k_1 \log \frac{I_1}{I_2} + k_2}{\log \frac{I_1}{I_2} + k_3 \log \frac{I_3}{I_2} + k_4}$$

This calculation can easily be carried out by means of the device according to the invention, as a result of this modular design referred to hereinbefore.

What is claimed is:

1. A photometric measuring device for automatically studying complex solutions with a variable background noise, wherein it comprises:
   a regulated light source providing a light beam for illuminating by means of an optical system a measuring cell adapted to contain a solution to be studied;
   means for splitting the light beam after it is affected by said solution into n individual light beams in which n is an integer higher than 2;
   balancing means for balancing the light intensity of each of said n light beams;
   means for making said n light beams monochromatic so as to associate with each of said n light beams a predetermined wavelength;
   a discriminator for distinguishing said n wavelengths from one another;
   a single detector able to transform the light beam from said discriminator into an electrical signal;
   an analog computing system responsive to said electrical signal for calculating the concentration of the most n−1 chemical species present in the solution; and
   means for the visual display of the results.

2. A photometric measuring device according to claim 1, wherein the discriminator is constituted by a first, solid half-cylinder of limited thickness not permitting the passage of light and whereby to the centre of the flat part of said half-cylinder is fixed a plane mirror and a second half-cylinder of the same size as the first and having four holes made in the rounded part of said second half-cylinder positioned in such a way that the light of a light beam entering by one of these holes is reflected by the plane mirror and leaves by another hole, there being at least four such holes.

3. A photometric measuring device according to claim 1 or 2, wherein the discriminator defining an axis of symmetry is able to rotate about its axis with a continuous movement in such a way as to permit, following the processing of light and then electrical information, to display curves of the concentration variation over a period of time of the at the most n−1 chemical species present in the solution to be studied.

4. A photometric measuring device according to claim 1, wherein the discriminator is constituted by a first member able to rotate with respect to a second fixed member in which are located n optical fibres, one of the ends of each of these fibres issuing to the outside of said second member facing the first member, the first member being provided with an opening which can be brought selectively in front of the said end of each of the optical fibres, the latter being joined to form a single optical fibre and at their other end so as to connect the discriminator to the detection means, then constituted by a single detector making it possible to sequentially determine the concentration of the at the most n−1 chemical species present in the solution to be studied.

5. A photometric measuring device according to claim 1, wherein the discriminator comprises a locating device making it possible to locate the light beam from the discriminator, said locating device being connected electrically to the analog computing system and making it possible to start the calculations associated with the reflected beam.

6. A photometric measuring device according to claim 1, wherein the means for splitting the light beam from the source into n individual light beams are constituted by n−1 splitting plates arranged one behind the other and inclined by 45° relative to the beam from the source and by plane mirrors making it possible to direct the n beams onto the discriminator.

7. A photometric measuring device according to claim 1, wherein the means for making each light beam monochromatic are constituted by fixed interference filters, corresponding to a predetermined wavelength gap ($\lambda \pm \Delta\lambda$) and adapted to the desired type of measurement.

8. A photometric measuring device according to claim 1, wherein the means for making each light beam monochromatic are constituted by monochromators.

9. A photometric measuring according to claim 1, wherein the analog computing system has a modular characteristic making it possible to calculate an expression of form:

$$K \log \frac{(I)_\alpha}{(I)_\beta}$$

in which k represents an attenuation coefficient $(I)_\alpha$, the light intensity corresponding to the wavelength $\lambda_\alpha$ and $(I)_\beta$ the light intensity corresponding to the wavelength $\lambda_\beta$.

* * * * *